(12) United States Patent
Merckx

(10) Patent No.: US 10,441,240 B2
(45) Date of Patent: Oct. 15, 2019

(54) METHOD AND SYSTEM FOR CONFIGURING AN X-RAY IMAGING SYSTEM

(71) Applicant: AGFA NV, Mortsel (BE)

(72) Inventor: Gert Merckx, Mortsel (BE)

(73) Assignee: AGFA NV, Mortsel (BE)

( * ) Notice: Subject to any disclaimer, the term of this patent is extended or adjusted under 35 U.S.C. 154(b) by 305 days.

(21) Appl. No.: 15/319,810

(22) PCT Filed: Jun. 29, 2015

(86) PCT No.: PCT/EP2015/064692
§ 371 (c)(1),
(2) Date: Dec. 19, 2016

(87) PCT Pub. No.: WO2016/001135
PCT Pub. Date: Jan. 7, 2016

(65) Prior Publication Data
US 2017/0135668 A1 May 18, 2017

(30) Foreign Application Priority Data

Jun. 30, 2014 (EP) .................................. 14174919

(51) Int. Cl.
*H05G 1/26* (2006.01)
*G01N 23/04* (2018.01)
(Continued)

(52) U.S. Cl.
CPC ............ *A61B 6/547* (2013.01); *A61B 6/0457* (2013.01); *A61B 6/08* (2013.01); *A61B 6/542* (2013.01); *A61B 6/545* (2013.01)

(58) Field of Classification Search
CPC ........ A61B 5/0077; A61B 5/0033; A61B 5/00
See application file for complete search history.

(56) References Cited

U.S. PATENT DOCUMENTS

2009/0122960 A1  5/2009 Maack et al.
2011/0249792 A1  10/2011 Lalena et al.
(Continued)

FOREIGN PATENT DOCUMENTS

JP        08-033621 A     2/1996
JP      2008-264519 A     11/2008
(Continued)

OTHER PUBLICATIONS

Official Communication issued in International Patent Application No. PCT/EP2015/064692, dated Oct. 8, 2015.

*Primary Examiner* — Don K Wong
(74) *Attorney, Agent, or Firm* — Keating and Bennett, LLP

(57) ABSTRACT

A method of monitoring a radiation amount received from an X-ray source in an X-ray imaging system for taking an X-ray image of an object includes the steps of obtaining one or more depth images from one or more depth cameras; the one or more depth cameras covering at least an area covered by an X-ray bundle of an X-ray source of the X-ray imaging system; positioning the object against or on a surface including radiation measurement chambers and identifying select radiation measurement chambers underneath the object from the one or more depth images and/or from a single depth image derived from the one or more depth images; and activating the select radiation measurement chambers.

16 Claims, 8 Drawing Sheets

(51) Int. Cl.
*A61B 6/00* (2006.01)
*A61B 6/04* (2006.01)
*A61B 6/08* (2006.01)

(56) References Cited

U.S. PATENT DOCUMENTS

| | | |
|---|---|---|
| 2014/0016750 A1 | 1/2014 | Kang et al. |
| 2014/0112441 A1 | 4/2014 | Becker et al. |
| 2014/0355735 A1* | 12/2014 | Choi ................. A61B 6/544 378/8 |

FOREIGN PATENT DOCUMENTS

| | | |
|---|---|---|
| WO | 2006/024622 A1 | 3/2006 |
| WO | 2014/033614 A1 | 3/2014 |

* cited by examiner

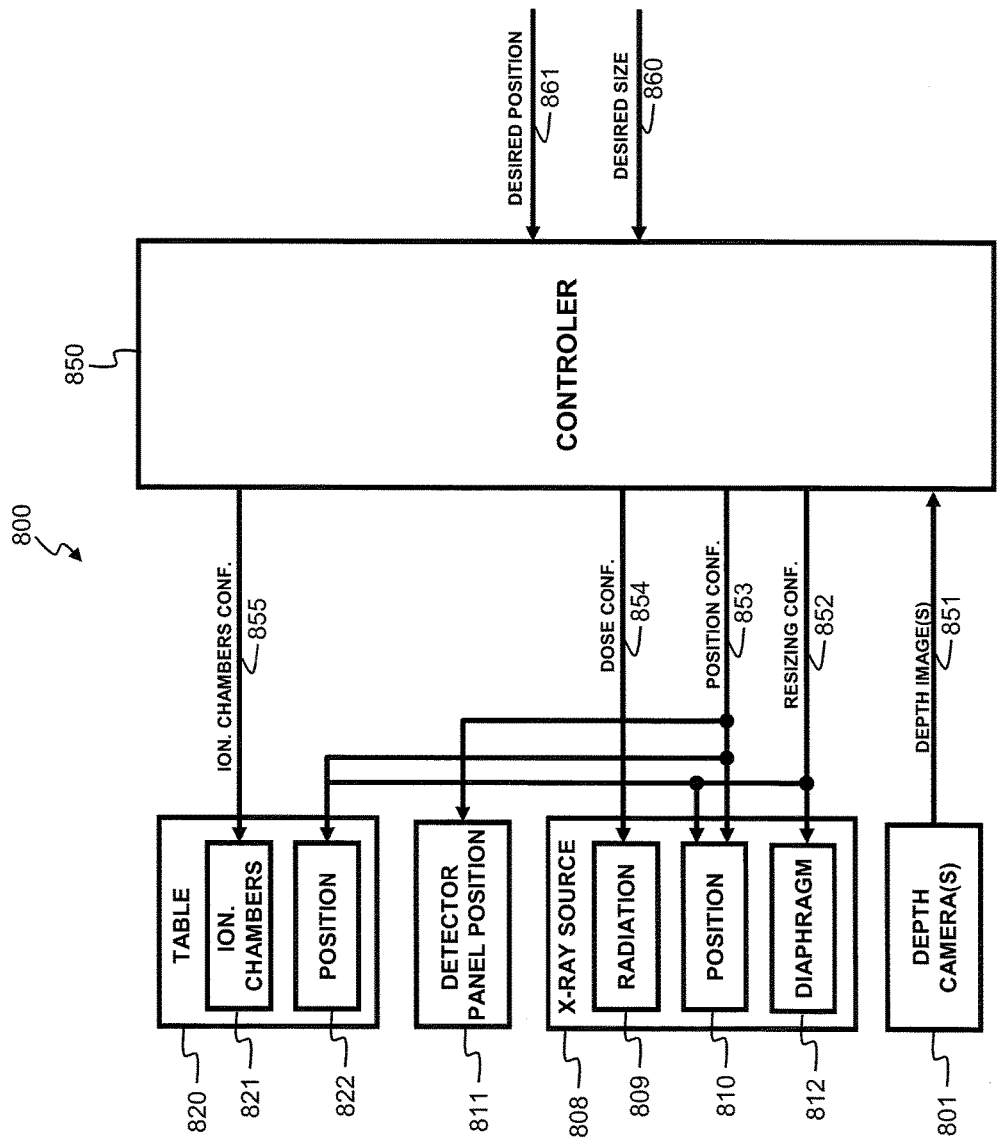

METHOD AND SYSTEM FOR CONFIGURING AN X-RAY IMAGING SYSTEM

CROSS REFERENCE TO RELATED APPLICATIONS

This application is a 371 National Stage Application of PCT/EP2015/064692, filed Jun. 29, 2015. This application claims the benefit of European Application No. 14174919.2, filed Jun. 30, 2014, which is incorporated by reference herein in its entirety.

BACKGROUND OF THE INVENTION

1. Field of the Invention

The invention relates to the field of X-ray imaging systems and more particular relates to the monitoring of a radiation amount received from an X-ray source in an X-ray imaging system. The invention further relates to the automatic obtaining of a configuration of such X-ray imaging systems. Such a configuration comprises a resizing configuration in order to get the object that is imaged with a certain size in the X-ray image. Such a configuration may also relate to a position configuration defining what will be in the centre of the captured X-ray image, typically an object of interest. Such a configuration may further relate to a dose configuration defining the radiation parameters of the X-ray source.

2. Description of the Related Art

Medical imaging systems usually include some user controls to adjust imaging parameters. The required configuration values are determined by a series of inputs, including the type of the study being performed and the characteristics of the subject being imaged. The exact radiation amount that is received from an X-ray source at given settings in a given configuration is preferably monitored. The process of selecting the right configuration given a certain subject and a desired study is crucial since this affects the image quality and the subject's wellbeing directly. In the case of X-ray imaging, for instance, image retakes caused by and erroneous configuration are especially undesirable due to the harmful nature of X-ray radiation to the subject.

In a traditional setting, the configuration is manually controlled by the operator. The radiation dose is typically derived from the medical study type and the size of the subject. The position configuration and resizing configuration of the system is typically done manually by sight, i.e., collimator setting and position of the X-ray source and detector panel are determined by the operator. However, this process is time consuming and prone to errors because the operator has no clear view of the applied adjustments. This results in an inefficient use of the X-ray system and a risk that multiple X-rays have to be captured.

Solutions have already been proposed to make the imaging process more efficient and less prone to errors.

In WO2006024622A1 an X-ray imaging system is proposed where cameras are used to capture images of the subject to be imaged. Either volume parameters are obtained from the 2D image data or a 3D model is obtained from the 2D images. From the volume parameters, the X-ray imaging system's configuration is derived in an automated way. A disadvantage of this system is that parameter extraction from the 2D images is not always correct, especially not when the cameras are under a large different angle than the X-ray source. Another disadvantage is that 3D model composition from 2D images is a processor intensive operation.

US20140016750A1 discloses an X-ray imaging system where depth cameras are used to obtain location information of the subject and to automatically position the X-ray emitter in the correct location. It is however a disadvantage that only the position can be configured. It is further silent on how the position configuration is to be achieved. It only provides details on the further use of markers which add complexity to the X-ray imaging system equipment.

SUMMARY OF THE INVENTION

Preferred embodiments of the invention overcome the above shortcomings and provide a method of monitoring a radiation amount emitted by an X-ray source and additionally providing an automated configuration of an X-ray system.

In a first aspect, a method of monitoring a radiation amount received from an X-ray source in an X-ray imaging system for taking an X-ray image of an object comprises the steps of obtaining one or more depth images (302, 502) from one or more depth cameras (101, 102, 201); the one or more depth cameras covering at least an area (103, 203, 303) covered by an X-ray bundle of an X-ray source (108, 208, 808) of the X-ray imaging system; and positioning the object against or on a surface comprising radiation measurement chambers (706); and identifying select radiation measurement chambers (710) underneath the object from the one or more depth images (702) and/or from a single depth image (702) derived from the one or more depth images; and activating the select radiation measurement chambers.

Such radiation measurement chambers are used for measuring the amount of received radiation and for ensuring that a sufficient dose was supplied in order to get a good X-ray image. These chambers may for example be ionization chambers.

It is an advantage that the correct chambers are automatically activated such that only the chambers under the object and/or under the subject measure the supplied dose. There is thus no manual verification step needed.

In a depth image, a pixel represents the distance between the depth camera and a closest object in front of the camera. Otherwise put, after applying lens correction, it may be transformed to a point cloud with the position of the camera as the origin of the coordinate system. These pixels may also be assigned other attributes through combination with input from different sensors. Such pixels may be visualized as points in a three dimensional or 3D space and colourized using information from the different sensors. The size of the object to be imaged is then determined from the one or more depth images. As the depth images also comprise depth information, a size can be determined in directions other than the ones in the depth image plane. This has the direct advantage that the size of the object as it will appear in the X-ray image under the current configuration of the X-ray system can be determined from the depth images, even if the cameras are under a different angle than the X-ray source.

If more than one depth camera is used, the multiple depth images may first be merged thereby obtaining the single depth image. The size of the object is then further obtained from this single depth image. This may for example be performed by forming a single point cloud from multiple depth images taking into account the spatial relation between the multiple depth cameras. The merging of depth images from different depth cameras allow integrating blind spots for some of the cameras into the single image.

When the size of the object is determined, it is known what the size of the object would be in the X-ray image under the current size configuration of the X-ray imaging system. From this size it is then determined how size configuration needs to be changed, i.e. by a resizing configuration, in order to have the size of the object in the X-ray image as desired. Typically, the desired size of the object is defined from a medical file. It may for example be defined that the object should fill the image as much as possible in order not to expose other tissue to the X-ray radiation. The relation between the size of the object in the depth images and the size of the object in the X-ray image under a certain configuration is derived from the geometric relation between the depth cameras and the other components of the X-ray imaging system, e.g., the X-ray source, the X-ray detector, a supporting table of the object.

It is an advantage that depth images are used for determining the size of the object as it avoids complex 3D modelling. It is not needed to construct first a three dimensional model to derive the size from a viewpoint different than that of the camera.

According to a preferred embodiment, the resizing configuration comprises a diaphragm reconfiguration of the X-ray imaging system.

A diaphragm or collimator reconfiguration may be used to limit the radiation to the object. For example, when the object is a knee, the diaphragm allows limiting the radiation to the knee. A smaller diaphragm thus creates a smaller image by limiting the borders of the image, i.e. it establishes a resizing of the object with respect to the obtained image itself.

Alternatively or additionally, the resizing configuration comprises a distance reconfiguration of the X-ray imaging system indicative for a reconfiguration of a distance between the X-ray source and the object.

By moving the X-ray source further or closer to the object, a respective zooming out or zooming in effect is obtained.

According to a preferred embodiment, the determining a resizing configuration comprises:

Determining a size of the area covered by the X-ray bundle of the X-ray source in the one or more depth images or in the single depth image derived from the one or more depth images.

Calculating a desired size of this area such that a size of the object with respect to this desired size of this area corresponds to the desired size of the object in the X-ray image.

Converting a difference between the desired size of the area and the size of the area to the resizing configuration by the known geometric relation.

This allows performing all operations on the depth images until a required change in size of the area is obtained. This size of the area in the image then directly relates to the needed resizing configuration.

According to a preferred embodiment, the method further comprises:

Determining a position of the object with respect to the area in the one or more depth images and/or in the single depth image derived from the one or more depth images, Determining a position change of the object relative to the area according to a desired position of the object with respect to the area.

Converting the position change to a position reconfiguration by the known geometric relation.

In other words, when the object is identified from the depth images, its position is localized. As there is a spatial relationship between the cameras and the X-ray source, the position of the object with respect to the X-ray source can be derived. The position of a known object defines the location of the object in space. The position may for example be specified by a location of a predefined point within or on that object and three rotational parameters, i.e., roll, pitch and yaw.

In X-ray imaging it is known what the object is and how it should be positioned according to the X-ray source, i.e., the desired position is known. This may for example be automatically obtained from a medical file or inputted by a user or operator. By the difference between the calculated position obtained from the depth images and the desired position, a position reconfiguration of the X-ray imaging system is calculated and applied. Such a position reconfiguration may comprise, a translation of the X-ray source, a rotation of the X-ray source, a translation of the object, a rotation of the object or any combination thereof.

It is thus an advantage the position configuration of the X-ray imaging system can be reconfigured based on one or more depth images without complex 3D modelling.

When the object is a part of a bigger object and the object falls outside the one or more depth images and the bigger object is partially in the one or more depth images and/or in the single depth image, then the determining the position of the object may advantageously comprise:

Determining a position of the bigger object with respect to the area in the one or more depth images and/or in the single depth image.

Deriving the position of the object from the position of the bigger object and a known position relation between the object and the bigger object.

When an object is initially positioned to have an X-ray taken, it is usually not in the correct position but may even fall outside the field of view of the one or more depth cameras. For example, if an image is to be taken of a person's leg, the one or more images may only show the upper body part of the person's body. This may occur when a person or object is initially positioned, but the system is still configured according to the setup for a previous object or person. In such a case, an operator could first roughly set up the system by sight such that the object falls within the one or more depth images. The advantage here is that this rough initial setup also becomes obsolete and, thus, the position configuration is completely automated.

When the object is a part of a human body comprising a skeleton and joints, then the determining the position of the object may, according to a preferred embodiment, comprise:

Determining a position of these joints in the one or more depth images and/or in the single depth image derived from the one or more depth images;

Deriving the position of the object from the position of the joints and a known position relation between the object and the joints.

In X-ray imaging, it is often the goal to image certain invisible body parts such as for example lungs, knees, heart . . . . These body parts cannot be directly derived from the depth images. Therefore, the position of the joints is first obtained from the depth images and then the position of the object is derived from the position of the joints. Deriving the position of joints from depth images is well known in the art and widely used in the field of gaming applications.

It is thus an advantage that an invisible object that is to be imaged can be positioned accurately and, therefore, no extra X-rays are needed in order to correct a wrongly positioned object.

According to a preferred embodiment, the resizing configuration and/or position configuration is applied as a last step. Thereafter, the steps may again be performed thereby performing the steps iteratively. This allows correcting inaccuracies introduced during a first iteration. For example, in the case where the object fell outside the depth image(s) in a first iteration, the obtained position or resizing configuration may be inaccurate. In a second iteration, the object may then fall within the depth images which allows configuring the system more accurately.

According to a preferred embodiment, the method further comprises:

Calculating a thickness of the object from one or more depth images or second set of depth images or from a single depth image obtained from the one or more depth cameras (or second depth cameras).

Converting this thickness to a dose configuration of the X-ray imaging system.

The thickness of the object, preferably along the optical axis of the X-ray source, is obtained from depth images. As the depth images comprise depth information, the thickness of the object may be directly derived from these images. This thickness then determines the dose to be delivered to the object in order to obtain a good X-ray image without delivering an overdose to the object.

It is an advantage that depth images from depth cameras are used as these allow to obtain the thickness information directly from the images. It suffices to change the view point of the point cloud which is implicitly present in depth images in order to get the thickness. Again, there is thus no need to first derive complex 3D models or surfaces from the image(s). In combination with the thickness, prior knowledge on the expected tissues in the planned study type can be used to predict x-ray attenuation, and hence the required dose.

It is a further advantage that the required dose is obtained. This allows a faster configuration of the system with less manual steps from a user or operator resulting in a more efficient use of the X-ray imaging system.

Preferably, the calculating the thickness and the converting the thickness is performed after the applying of the size reconfiguration and/or position reconfiguration. This has the advantage that at the moment of calculating the dose configuration, the object is already in its corrected position according to the X-ray source. The thickness may then be derived from the images along the current optical axis of the X-ray source.

The one or more depth images used for configuration and for thickness determining may be the same set or another set (obtained by same of other depth cameras). In other words, the resizing configuration, the dose configuration and/or position reconfiguration may thus be performed based on the same set of depth images. In this case it has to be taken into account from where the image will be taken according to the calculated position reconfiguration. This has the advantage that only one set of depth images needs to be taken resulting in a faster configuration of the system.

The calculating the thickness may further comprise calculating a distance between a point on the object and a background behind the object wherein the background is at a known distance from the object.

This has the advantage that the one or more depth cameras do not have to cover the complete object, i.e., the front and the back of the object, in order to calculate the thickness. It suffices to capture depth information about one side of the object and then to derive its thickness from the distance between the one side and a known background. More specifically, the background may be a surface against which or on top of which the object is positioned. This way the difference in depth between the front side of the object and the surface is a direct measure of the thickness. Such a surface may for example be the detector panel itself or a supporting table on or against which the object is positioned.

Advantageously, the one or more depth cameras comprise an aligned camera comprising an optical axis substantially aligned with an optical axis of the X-ray source.

This way, the image from the aligned camera forms an image with a field of view equivalent to or comprising the field of view of the X-ray source. This has the advantage that the thickness of the object may be directly derived from the depth values in the depth image of the aligned camera. Similarly, a position change of the object within the depth image may be easily transformed into a translation of the X-ray imaging system.

According to a second aspect, the invention relates to a X-ray imaging system for taking an X-ray image of an object comprising:

An X-ray source.

One or more depth cameras covering at least an area covered by an X-ray bundle of the X-ray source and configured to capture one or more depth images, Radiation measurement chambers, A controller further configured to:

Calculate a single depth image from the one or more depth images,

Identify select radiation measurement chambers underneath the object from the one or more depth images or from a single depth image derived from the one or more depth images, Activate the select radiation measurement chambers.

BRIEF DESCRIPTION OF THE DRAWINGS

FIG. 8 illustrates a schematic view of an X-ray imaging system according to a preferred embodiment of the invention.

DETAILED DESCRIPTION OF THE PREFERRED EMBODIMENTS

Figure 1:
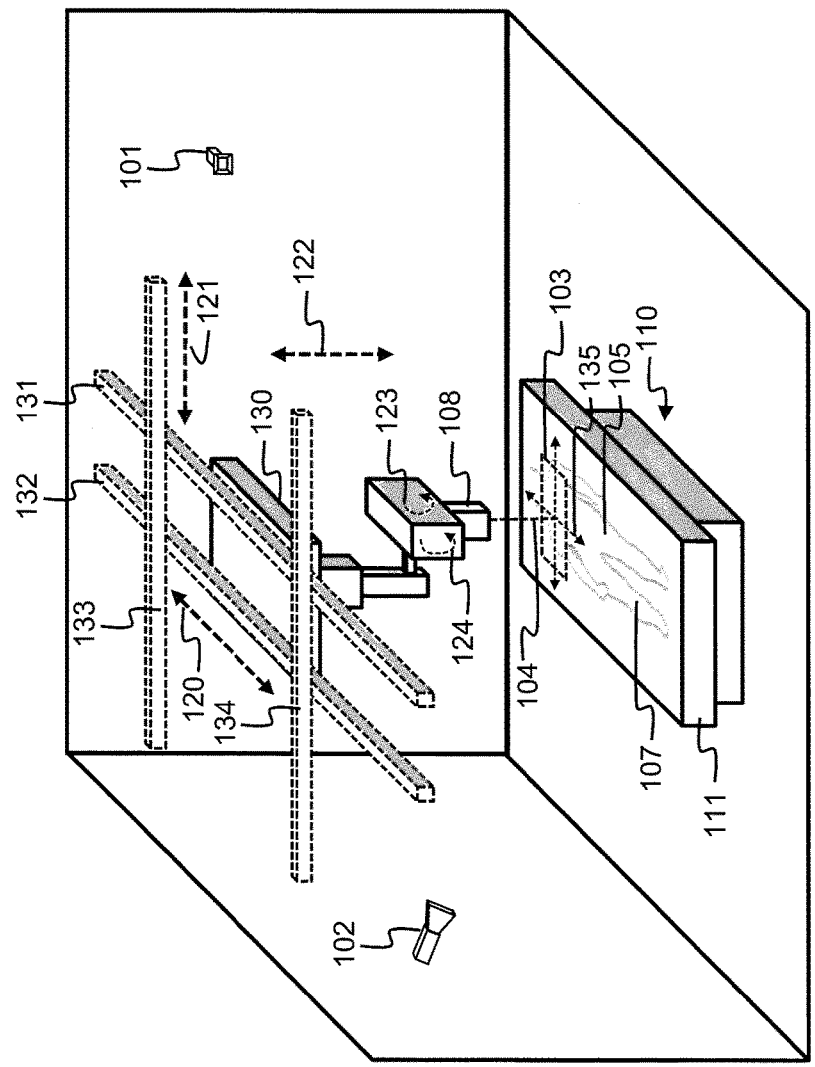
FIG. 1 illustrates parts of an X-ray imaging system according to a preferred embodiment of the invention.

FIG. 1 illustrates parts of an X-ray imaging system according to a preferred embodiment. The system comprises an X-ray source 108 or X-ray tube 108 to radiate a subject 105 in order to obtain an X-ray image. The area 103 illustrates the area that would be radiated by the X-ray bundle from the X-ray source 108 in the illustrated setup. This bundle is emitted from the X-ray source 108 along its optical axis 104. It is an object to configure the X-ray imaging system such that the appropriate area on the subject 105 is radiated and thus imaged or, in other words, to configure the X-ray system such that the area 103 at least covers the object 107 to be imaged. The configuration of the X-ray device will be illustrated in the preferred embodiments below for the case where an object 107, i.e., the knee of the subject 105, i.e., a person, is to be imaged. According to the example, it is thus the object to have the have the object 107 within the X-ray bundle, i.e., within the area 103. The X-ray bundle is then detected by an X-ray detector panel 111 behind the subject 105. Such a detector panel may for example be a digital flat panel detector for directly capturing a digital version of the image.

The X-ray imaging system according to the preferred embodiment further comprises depth cameras 101 and 102. The depth cameras are positioned and configured such that their field of view comprises the area 103 captured by the X-ray source 108. According to further preferred embodiments, the depth cameras are used for configuring the X-ray system.

The X-ray imaging system comprises several ways of configuration in order to manipulate or change the radiated area 103 and thus the field of view of the X-ray image.

A first type of configuration is a resizing configuration. By a resizing configuration, the size of the area 103 is defined and, thus, the size of the object 107 within the X-ray image is determined.

In a first way, the resizing configuration may be implemented by a configuration of the collimator or diaphragm. Typically such collimator is in front of the X-ray source and limits the X-ray bundle to a certain shape. This allows resizing the radiation area 103 on the subject 105 and thus limiting the amount of received radiation to the subject.

In a second way, the resizing configuration may be implemented by a configuration of the distance of the X-ray source 108 to the subject 105 and thus to the object 107, i.e. a distance configuration of the X-ray imaging system. The closer the X-ray source 108 is to the subject 105, the smaller the radiated area 103 becomes. This distance configuration may be accomplished by moving the X-ray source, by moving the supporting table 111 or by moving both along the axis 122.

A second type of configuration is a position configuration or position reconfiguration. By a position reconfiguration, the position of the target area 103 on the subject 107 is changed. A position reconfiguration may be implemented by a translational configuration, a rotational configuration or a combination of both.

In a translational reconfiguration of the X-ray imaging system, a translational movement 135 of the X-ray source 108 with respect to the subject 107 is performed and more specifically in a plane parallel to the detector 111. In the system of FIG. 1, such a translational movement or translational position configuration may be accomplished by a movement of the X-ray source 108 supporting assembly 130 along the guides 131 till 134. The guides 131 and 132 allow a movement in a first direction 120 and the guides 133 and 134 allow a movement in a second direction 121. Any combination of movements along these two directions 120 and 121 then define a translational position correction of the X-ray source 108. A translational position configuration may also be done by a movement of the supporting table 110 on which the subject 105 is positioned. A translational movement may also be done by a combination of a movement of the X-ray source 108 and a movement of the supporting table 110. A translational movement of the X-ray source 108 with respect to the subject 105 will result in a repositioning of the radiation area 103 on the subject.

By a rotational position configuration the X-ray source 108 rotates with respect to the subject 105 in order to image the object 107 from a different angle. Preferably, the X-ray source then rotates around the point where the optical axis 104 crosses the surface of the subject 105 resulting in a pure change in viewing angle without changing the field of view itself. This may be accomplished be a rotation 123 and/or 124 of the X-ray source 108 around itself combined with a movement of the X-ray source along the three directions 120, 121 and 122. This may also be accomplished by a small rotation of the supporting table 110 or by a combined movement of the supporting table 110 and the X-ray source 108.

A third type of configuration is a dose configuration. According to this configuration, the radiation parameters of the X-ray source 108 are configured. These parameters may comprise the current delivered to the X-ray source, the voltage delivered to the X-ray source and the exposure time.

Figure 2:
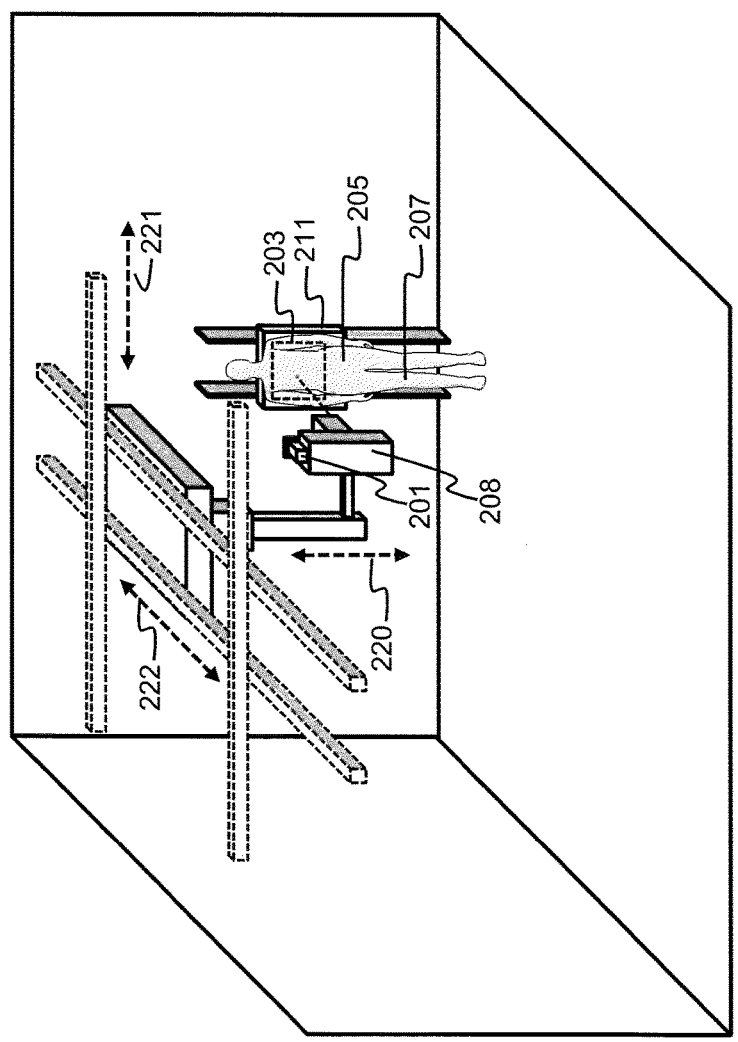
FIG. 2 illustrates parts of an X-ray imaging system according to a preferred embodiment of the invention.

FIG. 2 illustrates parts of an X-ray imaging system according to an alternative preferred embodiment. The X-ray detector panel 211 is in a vertical position and the subject 205 stands in an upright position against the detector panel. For the translational movement, the X-ray source 208 moves together with the detector panel 211 along the directions 220 and 221. For the distance configuration the X-ray source moves along the direction 222 further or closer to the subject 205 and thus the object 207. Also here, the area 203 covered by the X-ray bundle in the current setup of the X-ray system is shown on the subject 205. The X-ray system further also allows configuring the collimator or diaphragm in the X-ray source 208. Attached to the X-ray source 208 is a depth camera 201 covering at least the area 203. Preferably, the optical axes of the X-ray source 208 is aligned or substantially parallel to the optical axis of the depth camera 201.

According to a preferred embodiment, the three above identified configurations are automatically determined based on depth images acquired from depth cameras 101, 102, 201.

The depth images are a 2D image where each point in the image represents a distance value between the depth camera and the subject in front of it. The depth images may be combined with colour or infrared sensor information. The depth image may also be transformed to a point cloud where each point of the image is represented by a 3D coordinate. Such a transformation may already be performed in the depth camera itself.

When there is more than one depth camera such as in the preferred embodiment of FIG. 1, the depth images are merged into a single point cloud representation. This can be done be transforming the coordinate systems of each point cloud to a single fixed coordinate system. For the transformation, the known position relationship between the depth cameras and the X-ray imaging system is taken into account.

Figure 3:
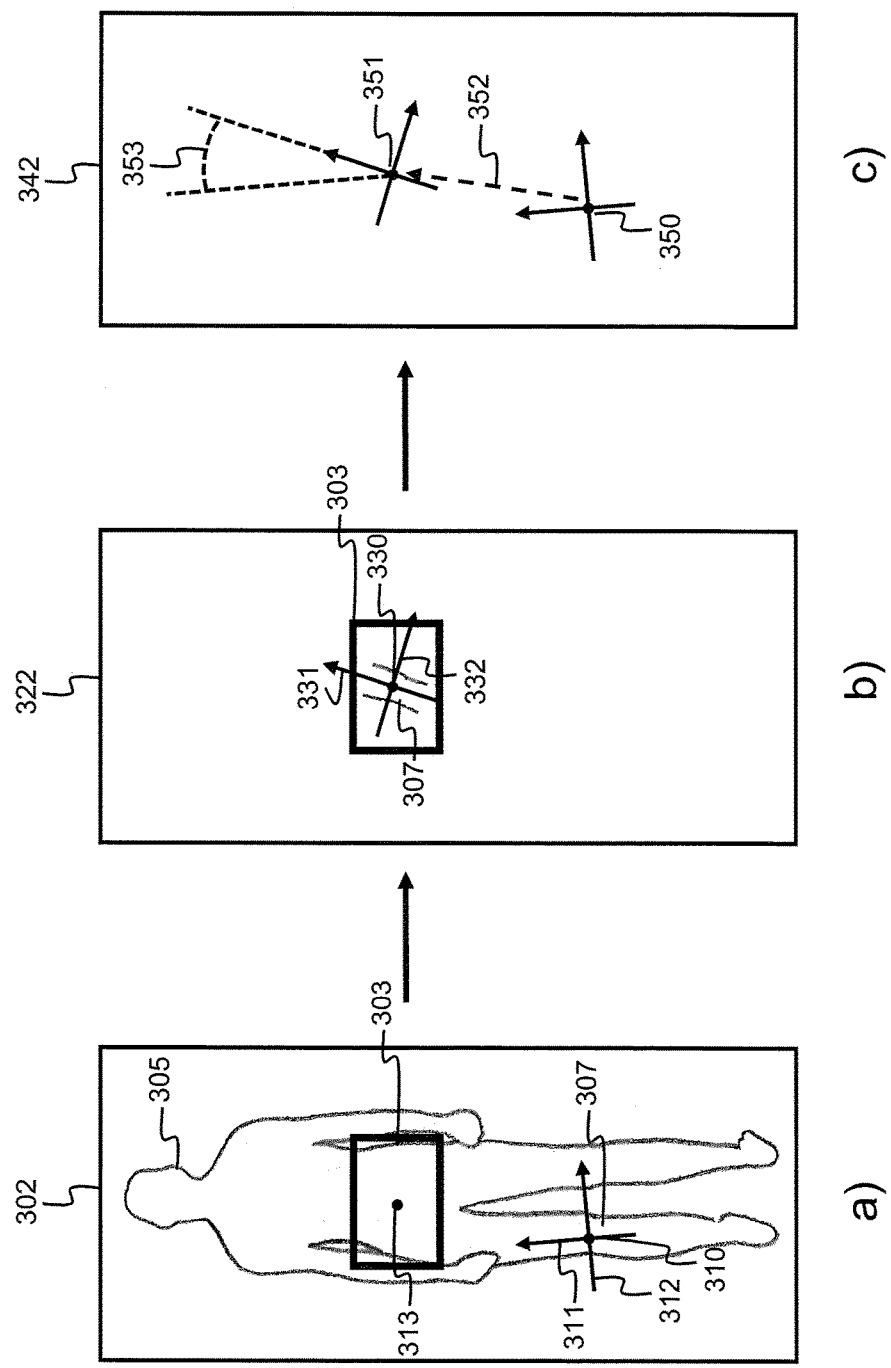
FIG. 3 illustrates steps performed for obtaining a resizing and position configuration of an X-ray imaging system from one or more depth images.

FIG. 3 illustrates how a configuration of the X-ray imaging system according to FIG. 1 or FIG. 2 is obtained from a depth image or merged depth image 302 obtained from the depth cameras 101 and 102 or 201. In the depth image 302, the subject 305, a person in this example, is represented. The purpose is to take an X-ray image of an object 307, in this case the knee 307 of the person 305. The rectangle 303 defines the current area 303 covered by the current configuration of the X-ray imaging system. In other words, if an X-ray would be taken with the current setup, the X-ray source would radiate the area 303 of the person 305 by its X-ray bundle. The area 303 is known in the depth image 302 by the known relationship between the X-ray source and the depth cameras and the known distance between the X-ray source and the subject. This distance may be derived from the point 313 on the depth image where the optical axis of the X-ray source coincides with the subject 305.

From the depth image 302, the object 307 is then identified and located. The definition of the object to be imaged may be retrieved from a medical file or selected by a user or operator of the X-ray imaging system. The location of the object may for example be defined by the location of a predefined origin 310 of the object 307 and the axes 311 and 312. Preferably there is also a third axis thereby defining the object within the depth image 302 in all three dimensions. This third axis is not shown in FIG. 3 for the sake of readability. From the depth image 302, the X-ray system thus obtains the location of the object 307 with respect to the depth image 302 itself. To identify the object 307, the system may use image recognition software which is available on the market for the processing of depth images. To derive information about the object or subject a recognition algorithm may be used such as the one disclosed in the publication Shotton, Jamie, et al. "Real-time human pose recognition in parts from single depth images." Communications of the ACM 56.1 (2013): pg. 116-124.

When the object that is to be imaged is identified and located in the depth image 302, the system retrieves the desired position of the object 307 with respect to the depth image. This is illustrated by the depth image 322 in FIG. 3-b). There the object 307 is located in its desired location defined by the origin 330 and the three axes of which two are shown as 331 and 332. This desired position may be retrieved from a medical file or database or may be inputted by a user or operator. The depth image 342 then illustrates the actual position 350 of the object as derived from image 302 and the desired position 351 as obtained from the view 322. The difference between the actual position 350 and the desired position 351 then determines a correction for the configuration of the X-ray imaging system.

This correction may be split in a translation 352 and a rotation 353 of the object with respect to the X-ray source. As the relation between the field of view of the depth image and the X-ray source is known, the corrections 352 and 353 are then translated into the actual position configuration of the X-ray system. The actual position configuration may be performed by a repositioning of the X-ray source with respect to the object 307, by a repositioning of the object 307 with respect to the X-ray source or by a combination of both.

In other words, for adjusting the X-ray imaging system according to the correction, a transformation between the imager coordinate system and the depth camera coordinate system is needed. Such information may be obtained by calibration or machine learning techniques such as adaptive filtering. After this transformation, the actual position configuration of the X-ray imaging system is known and is then applied by computing and sending specific control signals to the system's actuators.

From the depth images, also the resizing configuration is obtained. With respect to the depth images, the resizing may be represented by resizing the area 303 with respect to the object 307 which is equivalent to a resizing of the object 307 in the depth image if the area 303 remains the same size. This is also illustrated by FIG. 3 where the size of the actual object 307 in the depth image 302 in FIG. 3-a) is greater than the size of the object in its desired position as illustrated by FIG. 3-b) en -c). In order to achieve this, there are two possibilities for configuring the X-ray imaging system accordingly.

In the first way of implementing the desired resizing, the collimator size or aperture of the X-ray source is adapted. By making the aperture of collimator smaller, the radiated area will be smaller; and by making it bigger, the radiated area will be greater. The change in the opening of the collimator and thus the configuration of the collimator is directly related to the difference in the size of the actual object in the depth image and the desired of the object in the depth image in the target area and to the distance between X-ray source and the object 307. The change in size of the area to be radiated on the subject is then determined from this difference in size and from the distance between the object and the X-ray source. From this change in size and by the known geometric relation between the depth cameras and the position of the diaphragm or collimator in the X-ray source, the change in the opening of the collimator or change in diaphragm is derived.

In the second way of implementing the desired resizing, the distance between the X-ray source and the object 307 is changed. By decreasing the distance, the target area will become smaller and by increasing the distance, the target area will become bigger. Therefore, the distance configuration between the X-ray source and the object 307 is derived from the current distance and the change in size of the object.

Figure 4:
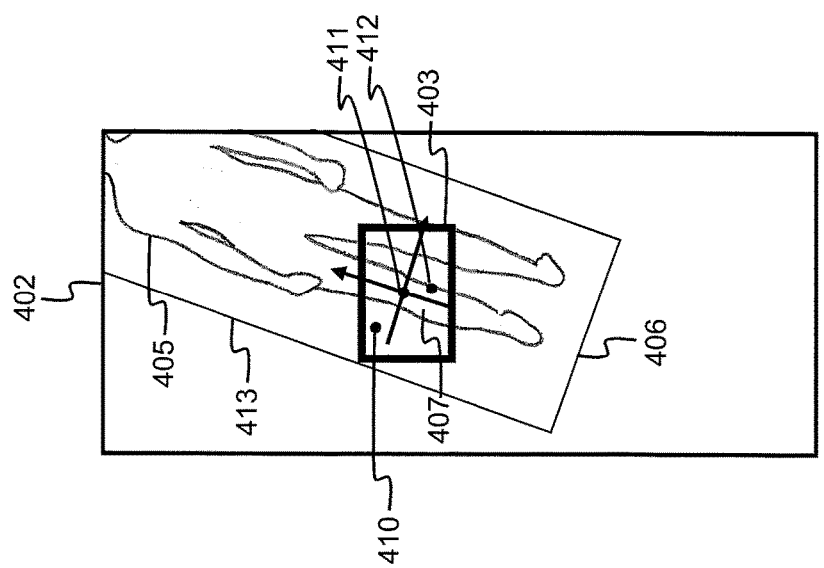
FIG. 4 illustrates steps performed for obtaining a dose configuration of an X-ray imaging system from one or more depth images.

After calculating the position configuration and the resizing configuration, the obtained configuration is applied to the X-ray imaging system. After applying the new configuration to the X-ray system, a new depth image is obtained from the depth cameras. This new depth image 402 is illustrated in FIG. 4. By way of example, the subject 405 is illustrated in its new position according to the target area 403. The object 407, i.e., the knee of the person 405, is now in its correct position 411 with the correct size with respect to the radiated area 403 for taking an X-ray image. In this position, the thickness of the object 407 is then obtained by deriving from the depth image 402 the distance to the point 412 in the area 403 that is the closest to the X-ray source and the distance to a known point 410. By the difference between the points 412 and 410, the thickness of the object 407 is obtained. This thickness then determines the actual dose that is to be delivered to the object 407 in order to obtain a good image without over-radiating the object 407. With the thickness, the transmission length of the X-ray bundle is known and together with the knowledge of the tissue that is being imaged, the exposure settings or dose configuration is derived as will be described later.

The known point 410 may for example be a point on a flat surface 413 behind the subject 405. If the subject is positioned against this surface 413, the thickness is the actual difference between the depth values of the respective locations 410 and 412 in the depth image. The flat surface 413 may further be a table on which a subject 405 is placed. The flat surface 413 may also be the X-ray detector panel of the X-ray imaging system.

According to a preferred embodiment, the dose, resizing and position configuration is performed in a single step, i.e., these configurations are derived from the same set of depth images. For the dose configuration, the thickness of the object is derived after that the position configuration is obtained. From the position configuration it is known from which side the object will be radiated. The thickness of the object is then calculated according to the irradiation direction after the geometric configuration would be applied.

Figure 5:
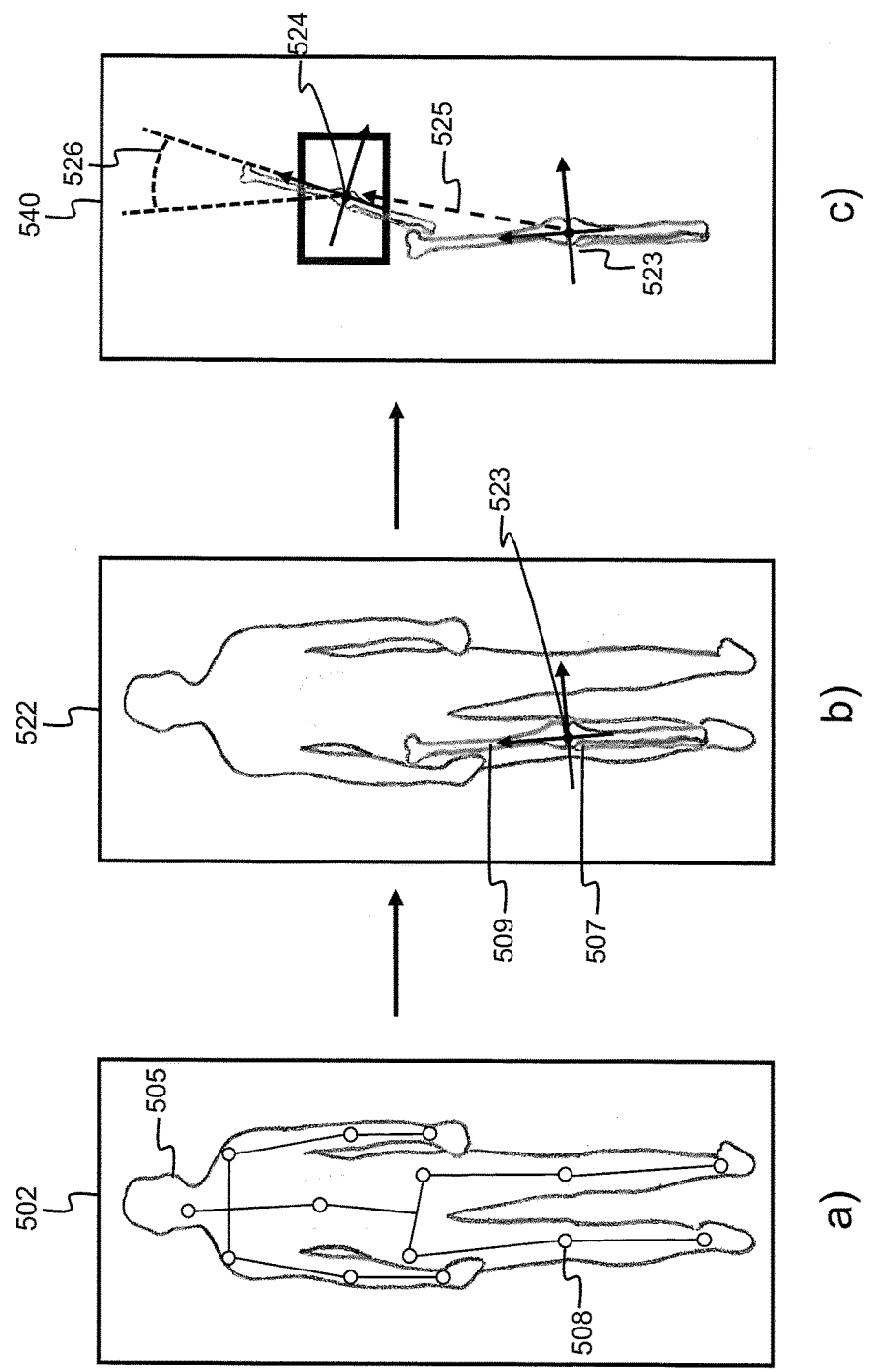
FIG. 5 illustrates steps performed for obtaining a resizing and position configuration of an X-ray imaging system from one or more depth images when the object is not visible on the depth image.

In most cases an X-ray image is taken to obtain information about an inner object of a person such as for example a bone or an organ. In such a case, the object itself will not be visible in the depth images. FIG. 5 illustrates how the geometric configuration of the X-ray imaging system may be derived from the depth image 502 according to a preferred embodiment. In the example of FIG. 5, the object is the knee bones 507 of the person 505. From the depth image 502, the location of the joints 508 is identified in the depth image 502. This may for example be done by image recognition software as available on the market, for example by using the Kinect Software Development Kit or SDK proved by Microsoft. From the location of the joints 508, a skeleton or part of the skeleton 509 comprising the object 507 is then fitted on the depth image as illustrated by depth image 522 in FIG. 5. From this skeleton 509, the location 523 of the bone structure, i.e. the knee bones 507, is derived. Then, the difference in location is obtained between the actual location 523 of the object and the desired location 524 of the object 507 as shown in the schematic view 540 of the depth image. Similar to FIG. 3 this may be done be obtaining the translation 525 and the rotation 526.

Figure 6:
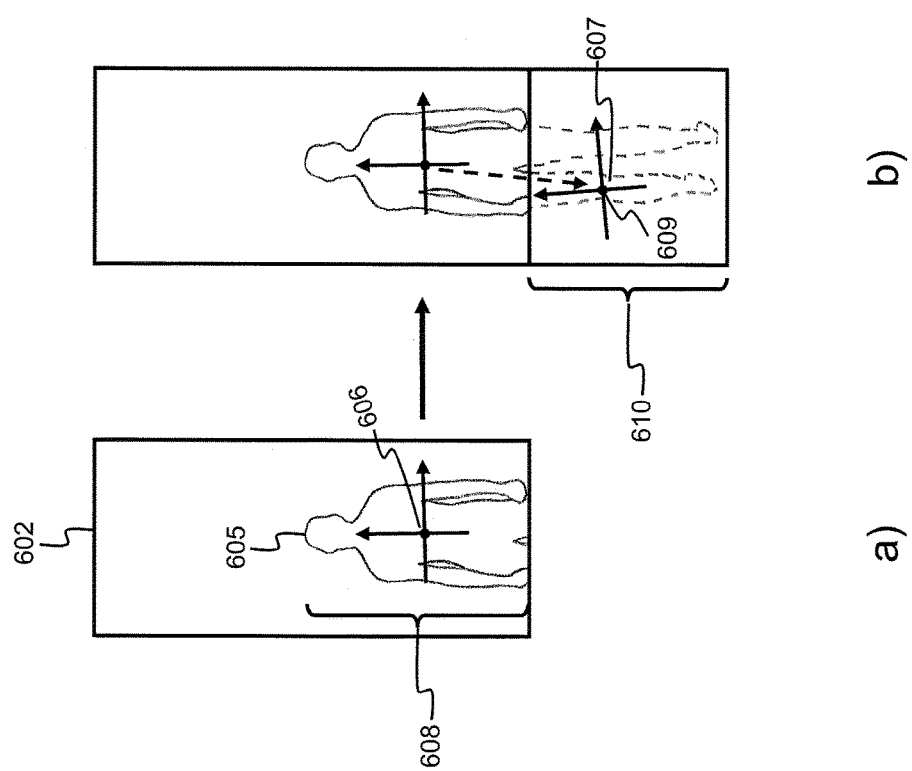
FIG. 6 illustrates steps performed for obtaining a resizing and position configuration of an X-ray imaging system from one or more depth images when the object is outside the depth image.

In some cases, the object 607 may fall outside the depth image as shown by FIG. 6. In the depth image 602, only the upper body part 608 of the subject 605 is represented. It is therefore not possible to derive the position of the object directly from the depth image 602. In order to do so, the position 606 of the body 605 is determined in a first step as illustrated in FIG. 6-a). In a second step, the position 609 of the object 607 is determined as illustrated in FIG. 6-b). This is done by using a known relation between the location 606 of the body and the location 609 of the body part 607. Knowing this relation, implies the use of anatomical prior knowledge. This can be provided by registering anatomically labelled 3D surface- or volumetric-reference data with the sensor data.

Alternatively, this may be done by extrapolating the depth image with object 607. In the example of FIG. 6 where the subject is a person, this may be done by identifying the upper body part 608 and then extrapolating the remaining part 610 of the body in the depth image. The object is then located in the extrapolated part 610. Similar steps may be used for obtaining the size of the object 607 as the size of the object is related with the size of the subject, i.e., the size of the person 605. The remaining steps for configuring the X-ray imaging system are then performed similarly as for the case of FIG. 3-b) and -c). Alternatively, a depth camera could be positioned such that it provides a view covering all possible positions an object could be initially positioned in thereby providing a bird's eye view of the X-ray system.

In one preferred embodiment the thickness information supplied by the 3d sensor is used to scale a model containing anatomical prior information of the body part under examination. The information on which body part is being imaged can be derived directly from the skeletonized 3d sensor data or from the chosen exam type. The scaling can be performed by applying an overall scaling or by registering the anatomic model to the 3D sensor data of the patient. The scaled anatomic model is then used to calculate the approximate transmission lengths of the rays through each of the tissue types in the anatomic model. The combination of the transmission lengths and tissue type attenuation factors can then be used to calculate accurate patient and pose specific exposure parameters. To prevent unfeasible dose settings a sanity check can be performed on the resulting dose parameters with customary dose parameters for the study type. The combination of the transmission lengths and tissue type attenuation factors can also be used to calculate dose settings for a specific wanted contrast ratio.

Figure 7:
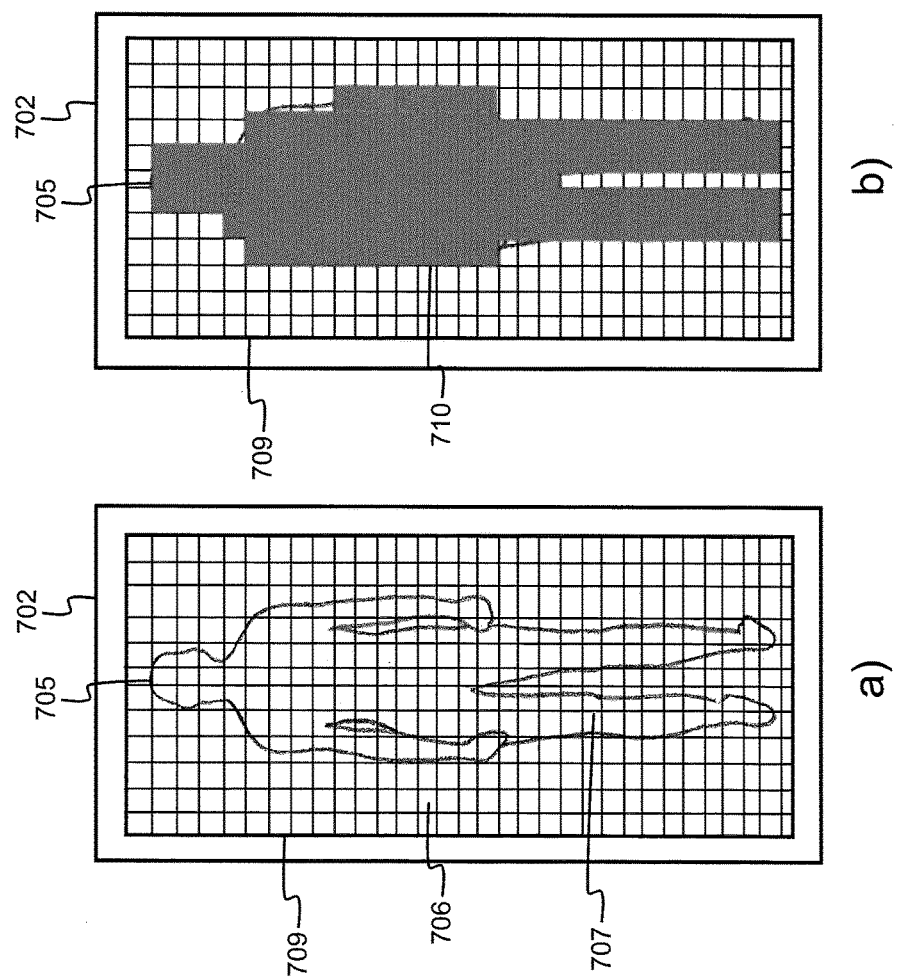
FIG. 7 illustrates steps performed for automatically selecting the correct radiation measurement chambers.

According to a preferred embodiment of the invention, the X-ray imaging system comprises a supporting table with ionization chambers. Each of these chambers is configured to measure the amount of radiation received from the X-ray source. The measured amount is then used for Automatic Exposure Control or AEC. If a sufficient amount of radiation is measured in the chambers underneath the object, the radiation is stopped and a sufficiently exposed X-ray image is guaranteed. In order for this to work correctly, it is necessary to only activate the chambers under the subject or the object. FIG. 7 illustrates how this is performed in an automated way using the obtained depth image 702. First the table 709 is identified in the depth image 702. This may be done by image recognition or by the known current position configuration of the table. From the position of the table 709, the position of the chambers 706 within the image is derived. From the depth image, also the area covered by the subject 705 and/or object 707 is derived. Then, only the chambers 710 that are covered by the subject 705 or object 707 are activated.

The steps performed for configuring the X-ray imaging system according to the above preferred embodiments may further be performed iteratively. After the configuring, i.e. position configuration, resizing configuration and dose configuration, a new set of depth images may be obtained and a new configuring is then performed. The position configuration and resizing configuration may be performed first in one or more steps followed by a dose configuration in the final step.

According to a preferred embodiment, the automated steps for configuring the X-ray imaging system according to the FIGS. 3 to 7 are performed on a controller 850 as illustrated in FIG. 8. The controller 850 as part of the X-ray imaging system 800 receives one or more depth images from the depth camera(s) 801. Then, according to the above preferred embodiments, it determines the resizing configuration 852, the position configuration 853, the dose configuration 854 and the configuration 855 for the ionization chambers. The controller takes further as inputs the desired position 861 and the desired size 860 of the object. These inputs may come from a medical file or medical database. The resizing configuration may be applied as a diaphragm setting 812 in the X-ray Source 808, as a distance setting 822 or 810 determining the distance between the subject on the table 820 and the X-ray source 808 or any combination of these. The position configuration 853 of the controller 850 may be implemented as a position setting 810 of the X-ray source 808 or as position setting 822 of the supporting table on which the object is positioned. Optionally, also the position of the detector panel 811 may be set accordingly. The dose configuration 854 is applied as a setting of the radiation parameters 809 in the X-ray source. The configuration 855 of the ionization chambers is then applied in the ionization chamber 821 of the table 820 supporting the subject and/or object. All steps performed in the controller 850 may be implemented in software that can be compiled to processor instructions. These instructions then run on a processor 850 in the controller upon execution.

Although the present invention has been illustrated by reference to specific preferred embodiments, it will be apparent to those skilled in the art that the invention is not limited to the details of the foregoing illustrative preferred embodiments, and that the present invention may be embodied with various changes and modifications without departing from the scope thereof. The present preferred embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and preferred embodiments of the invention are capable of operating according to the present invention in other sequences, or in orientations different from the one(s) described or illustrated above.

The invention claimed is:

1. A method of monitoring a radiation amount received from an X-ray source in an X-ray imaging system for taking an X-ray image of an object, the method comprising the steps of:
    obtaining one or more depth images from one or more depth cameras, the one or more depth cameras covering at least an area covered by an X-ray bundle of the X-ray source of the X-ray imaging system;
    positioning the object against or on a surface including radiation measurement chambers;
    identifying select ones of the radiation measurement chambers underneath the object from the one or more depth images and/or from a single depth image derived from the one or more depth images; and
    activating only the select ones of the radiation measurement chambers to measure the radiation amount received from the X-ray source.

2. The method according to claim 1, further comprising the steps of:
    determining a size of the object in the one or more depth images or in the single depth image obtained from the one or more depth images; and
    determining a resizing configuration of the X-ray imaging system from the size of the object, from a desired size of the object in the X-ray image, and from a known geometric relationship between the one or more depth cameras and the X-ray imaging system.

3. The method according to claim 2, wherein the resizing configuration includes a diaphragm reconfiguration of the X-ray imaging system.

4. The method according to claim 2, wherein the resizing configuration includes a distance reconfiguration of the X-ray imaging system indicative of a reconfiguration of a distance between the X-ray source and the object.

5. The method according to claim 2, wherein the step of determining a resizing configuration includes:
    determining a size of the area in the one or more depth images or in the single depth image;
    calculating a desired size of the area such that a size of the object with respect to the desired size of the area corresponds to the desired size of the object in the X-ray image; and
    converting a difference between the desired size of the area and the size of the area to the resizing configuration using the known geometric relationship.

6. The method according to claim 2, further comprising the steps of:
    determining a position of the object with respect to the area in the one or more depth images and/or in the single depth image;
    determining a position change of the object relative to the area according to a desired position of the object with respect to the area; and
    converting the position change to a position reconfiguration using the known geometric relationship.

7. The method according to claim 6, wherein the object is a portion of a bigger object, the object falls outside the one or more depth images, the bigger object is partially in the one or more depth images and/or in the single depth image derived from the one or more depth images, and the step of determining the position further comprises:
    determining a position of the bigger object with respect to the area in the one or more depth images and/or in the single depth image; and
    deriving the position of the object from the position of the bigger object and a known position relationship between the object and the bigger object.

8. The method according to claim 6, wherein the object is a portion of a human body including a skeleton and joints, and the step of determining the position of the object includes:
    determining a position of the joints of the skeleton in the one or more depth images and/or in the single depth image derived from the one or more depth images; and
    deriving the position of the object from the position of the joints and a known position relationship between the object and the joints.

9. The method according to claim 6, further comprising the step of:
    applying the resizing configuration and/or the position reconfiguration to the X-ray imaging system.

10. The method according to claim 9, wherein the steps are performed iteratively.

11. The method according to claim 1, further comprising the steps of:
    calculating a thickness of the object from the one or more depth images or from the single depth image obtained from the one or more depth cameras; and
    converting the thickness to a dose configuration of the X-ray imaging system taking into account a transmission length of the x-ray bundle emitted by the X-ray source through the object and knowledge about tissue types being imaged.

12. The method according to claim 11, wherein step of calculating the thickness and the step of converting the thickness are performed after a step of applying a resizing configuration and/or a position reconfiguration to the X-ray imaging system.

13. The method according claim 11, wherein the thickness is calculated along an optical axis of the X-ray source.

14. The method according to claim 11, wherein the step of calculating the thickness further includes:

calculating a distance between a point on the object and a background behind the object, and the background is at a known distance from the object.

15. The method according to claim 14, wherein the background is a surface against which or on top of which the object is positioned.

16. The method according to claim 1, wherein the one or more depth cameras includes an aligned camera including an optical axis aligned or substantially aligned with an optical axis of the X-ray source.

* * * * *